US008064571B2

(12) United States Patent  (10) Patent No.: US 8,064,571 B2
Thieberger et al.  (45) Date of Patent: Nov. 22, 2011

(54) METHOD AND ARRANGEMENT FOR IMPROVING TOMOGRAPHIC DETERMINATIONS, PARTICULARLY SUITABLE FOR INSPECTION OF STEEL REINFORCEMENT BARS IN CONCRETE STRUCTURES

(75) Inventors: Peter Thieberger, Brookhaven, NY (US); Mario Alberto Juan Mariscotti, Boulogne (AR); Marcelo Daniel Ruffolo, Caseros (AR); Teresita Frigerio, Capital Federal (AR)

(73) Assignee: Tomografia de Hormigon Armado S.A., Boulogne, Provincia de Buenos Aires (AR)

( * ) Notice: Subject to any disclaimer, the term of this patent is extended or adjusted under 35 U.S.C. 154(b) by 211 days.

(21) Appl. No.: 12/312,448

(22) PCT Filed: Oct. 31, 2007

(86) PCT No.: PCT/US2007/022868
§ 371 (c)(1),
(2), (4) Date: May 11, 2009

(87) PCT Pub. No.: WO2008/060398
PCT Pub. Date: May 22, 2008

(65) Prior Publication Data
US 2010/0054397 A1  Mar. 4, 2010

(30) Foreign Application Priority Data

Nov. 14, 2006 (AR) .................................. P060104990

(51) Int. Cl.
*G01N 23/04* (2006.01)

(52) U.S. Cl. .......................................... 378/57; 378/205
(58) Field of Classification Search .................... 378/57, 378/205
See application file for complete search history.

(56) References Cited

U.S. PATENT DOCUMENTS

| | | | |
|---|---|---|---|
| 5,828,723 A | 10/1998 | Mariscotti | |
| 5,960,058 A | 9/1999 | Baba et al. | |
| 6,049,586 A | 4/2000 | Kitaguchi et al. | |
| 6,324,248 B1 | 11/2001 | Timmer et al. | |
| 6,542,580 B1 * | 4/2003 | Carver et al. | 378/57 |
| 2002/0049378 A1 * | 4/2002 | Grzeszczuk et al. | 600/427 |
| 2005/0078787 A1 | 4/2005 | Dinten et al. | |
| 2005/0226375 A1 | 10/2005 | Eberhard et al. | |
| 2006/0054811 A1 | 3/2006 | Shemesh | |
| 2006/0056585 A1 | 3/2006 | Georgeson et al. | |

FOREIGN PATENT DOCUMENTS

| | | |
|---|---|---|
| JP | 7-151719 A | 6/1995 |
| JP | 2000-193611 A | 7/2000 |
| JP | 2001-041908 A | 2/2001 |

* cited by examiner

*Primary Examiner* — Hoon Song
(74) *Attorney, Agent, or Firm* — Cort Flint

(57) ABSTRACT

A method and arrangement for improving tomographic determinations by means of radiation, specially suitable for steel bars in concrete. The method comprising irradiating said body with penetrating radiation, recording said radiation transmitted through said body in recording means; providing a reference system with a plurality of independently identified and individualized reference elements made of a high density radiation-absorbent material, such reference elements being arranged in an orderly manner; identifying the above mentioned measurements; determining irradiation times; and determining the position and size of objects within a body based on the information recorded on the recording means used for measurement.

21 Claims, 6 Drawing Sheets

METHOD AND ARRANGEMENT FOR IMPROVING TOMOGRAPHIC DETERMINATIONS, PARTICULARLY SUITABLE FOR INSPECTION OF STEEL REINFORCEMENT BARS IN CONCRETE STRUCTURES

FIELD OF APPLICATION

The present invention relates to methods for analyzing the three-dimensional structure of a body opaque to visible light, using penetrating radiation, such as X-rays or gamma-rays, whose intensity is attenuated as a function of the product of the thickness times the density of the traversed matter. Particularly, the invention is intended for the analysis of structures, and especially for the determination of the position and diameter of steel bars in reinforced concrete structures, such as beams, columns, and slabs.

Experimental work carried out to this date has employed gamma-radiation sources. However, it is possible to apply the same method to cases in which X-ray tubes, linear accelerators, or other radiation sources are used, for the same as well as for other applications.

The present invention comprises a method for performing an automatic and accurate determination of parameters that are essential for a three-dimensional analysis, such as the position of the source and that of the transmitted-radiation recording means; an optimal arrangement for improving image quality when the recording means comprises a film which is sensitive to variations in radiation intensity; an arrangement for the tomographic determination of reinforcement bars in very thick pieces of concrete using low energy radioactive sources; and a procedure for obtaining a tomographic result from such measurements.

DESCRIPTION OF THE PRIOR ART

Tomographic techniques are extensively used in medicine. The present method is particularly suited, without limitation, for reinforced concrete, and may be extended to other applications. In this field, X-rays generated by conventional tubes, gamma-rays emitted by radioactive sources or high energy electromagnetic radiation generated by linear accelerators have been used for obtaining two-dimensional images of radiation transmitted through structural pieces of reinforced concrete, either using radiation-sensitive films (conventional or digital radiographic plates) (ref. 3), radiation-to-visible light fluorescent conversion screens (JP 61-254837, U.S. Pat. No. 6,333,962) or scintillation- or solid state-type radiation detectors (U.S. Pat. No. 5,933,473). The two-dimensional information obtained through the application of these techniques is useful for detecting metallic elements, the presence of corrosion therein, voids and cracks in a piece of concrete. The three-dimensional problem, that is, the determination of the position and diameter of steel bars in reinforced concrete structures, has also been dealt with, although without much progress so far (ref. 1, 2, 3, U.S. Pat. No. 5,828,723) except for the works described in ref. 4. Some of the problems associated with this type of measurements have not yet been solved. These problems are: the difficulties for acquiring data with proper accuracy regarding the position of the source and of the recording means required for the tomographic mapping of steel bars; the low contrast of images, and hence the difficulties involved in interpreting them, due to the intensity of scattered radiation, especially in the case of concrete pieces of considerable size; and the limitation in range of concrete thicknesses that may be studied using low energy portable sources.

The procedure for the tomographic determination of reinforcement bars, that is, for determining the position and diameter of steel bars in a reinforced concrete structure, consists, in a first step, in arranging the radiation source in a first position on one side of the structural element under study and the recording means on the other side approximately opposite to the location of the source during irradiation, such that the section under examination is comprised within the volume of a pyramid of height equal to the distance between the source and the recording means and base equal to the area covered by the recording means. In a second step, the element under examination is exposed to radiation emitted by the source during a period of time long enough for the recording means to receive the dose of transmitted radiation required to obtain an optimal contrast between the radiation transmitted through the steel bars and the radiation that has not traversed the steel bars. The amount of irradiation time is determined as a function of the product of the thickness times the density of the element under examination. In subsequent steps, the procedure is repeated, with the source, and sometimes the recording means, located at different positions such that the volume under examination is similar to that in the first step. Finally, the information recorded by the recording means is analyzed for all the measurements referred to a given structural piece, using a mathematical algorithm to obtain the position and diameter of steel bars inside the volume covered by the measurements.

In order to apply said mathematical algorithm it is necessary to know the positions of both the source and the recording means for the different measurements, referred to a coordinate system fixed to the structural piece under study.

The present invention improves the prior art regarding the above-mentioned requirement by providing:

a) the introduction of reference elements generating fiducial marks for greater accuracy, reliability and automation potential.

b) an arrangement of the recording means consisting in placing such means at a certain distance from the structural piece under study, thereby improving the quality of the information obtained. The optimum value for this distance is calculated using a Montecarlo-type simulation program specially developed for this purpose (ref. 6)

c) an arrangement of—elements to filter the scattered radiation, optimized by the above-mentioned Montecarlo-type program (ref. 6).

d) a methodology for analyzing the information recorded in the recording means for solving the tomographic problem, that is, the three-dimensional mapping of steel bars in a reinforced concrete structure that substantially improves the previous art.

The use of fiducial marks produced by radiation-absorbing reference objects that are recorded on a radiographic film or digital recording means for image aligning or calibrating purposes is well known in medical radiography (ref. 7) as well as in industrial X-ray determinations (ref. 5). In the first case, reference elements are incorporated into the patient's body in order to solve the problem derived from the change of position of the patient in different measurements. In the case of industrial X-ray determinations, for example, a sequence of radiation-absorbing bars of known dimensions is placed on the upper portion of a reinforced concrete slab in order to determine the thickness of the slab.

In the present invention, the use of fiducial marks serves the double purpose of improving both the accuracy and reliability of tomographic determinations of the location and size of steel bars in a reinforced concrete structure. In contrast to other industrial X-ray applications, the objects whose images are to be recorded on the radiography are generally located at a considerable distance from the recording means. Therefore, it is possible to obtain position data through stereoscopic reconstruction, by taking two or more exposures with the radiation source placed in different locations. For the reconstruction to be accurate it is important to know precisely the position of both film and source with respect to the structure under study.

SUMMARY OF THE INVENTION

In the method of the present invention, fiducial marks are recorded on the recording means, for example a radiographic plate, by placing radiation-absorbent reference objects on frames located on the radiation source side and/or the recording means side, in accurately known positions. The purpose of this is to minimize the need of manual measurements and recordings during fieldwork that are prone to error. In this way the information required for the tomographic determination is automatically recorded on the recording means for use in the subsequent computational analysis, thus preventing inaccuracies and errors characteristic of manual determinations, as well as others of the previous art, such as the position of the radiographic film inside the cassette where it is placed in order to avoid its exposure to light.

In addition to reference elements, in the method of the present invention the frame on the recording-means side includes an arrangement for positioning the recording means at an optimum distance from the structural element being examined. The frame also allows the addition of adequate filters for attenuating the effect of scattered radiation that, in the case of reinforced concrete, severely limits the quality of images. Both optimum distance and optimum filters are determined by means of a computer program specially developed for this purpose. Finally, the method comprises a specially developed procedure for carrying out the tomographic analysis, taking into account the fiducial marks and the conditions of frames and supports.

DETAILED DESCRIPTION OF THE INVENTION

Figure 1:
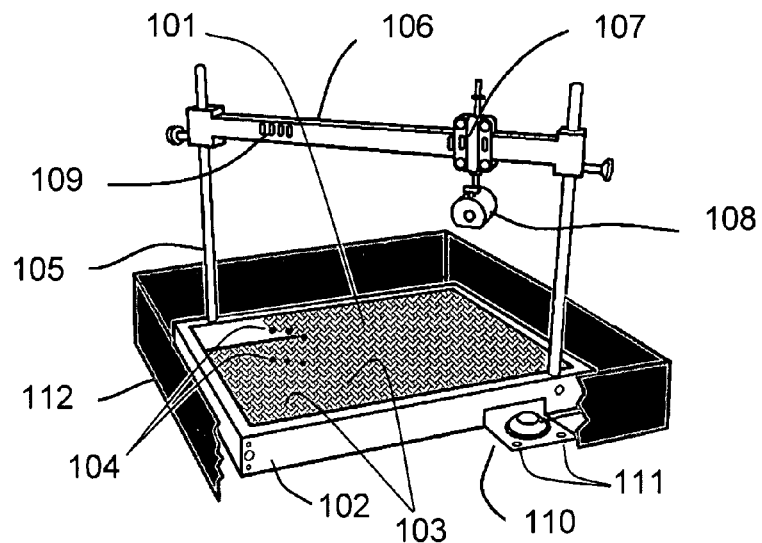
FIG. 1 is a perspective view of the "source assembly" used in an arrangement for determining the position and size of steel reinforcement bars in reinforced concrete slabs and walls.

The method of the present invention includes data collection equipment to be used in the field (the "field work") and a procedure for the analysis of such data to obtain the tomographic result. The equipment can be arranged in different ways according to the characteristics of the structural element under study, according to the description given below.

First the general aspects of the method are described and then an explanation is given about the manner in which the method is applied to different specific cases (inspection of slabs and walls, of beams and columns and other cases.)

The field equipment that is an object of the present invention comprises, in the first place, an assembly of devices on the radiation-source side, designated "source assembly". In the case of measurements using an "external source", that is, with the radiation source located externally to the piece under study, the "source assembly" comprises a support for the radiation source (X-ray tube, linear accelerator, radioactive source or other) with its corresponding collimator and a first rack, hereinafter called "rack I", detachably attached to said support, containing the reference elements. The "source assembly" can be provided with shielding elements. The rack comprises a frame made of a lightweight but strong material (such as, for example, Al), of rectangular shape or otherwise, two rigid plates having the same shape of the frame attached to said frame so as to cover both of its sides, such plates being made of poor radiation-absorbent material (such as for example some kind of plastic). The "source assembly" is fixed to one side of the body to be examined. If measurements are to be carried out using an "internal source", the method is applicable only if a radioactive tablet is used as a radiation source, and in such case the "source assembly"becomes simply a holder for the source container/projector and an "extension" that is introduced within the piece under study through a hole drilled therein, so that the radioactive tablet can be placed in different positions within the body under examination.

Secondly, the equipment comprises a second rack, hereinafter called "rack II", located on one of the sides of the piece under study opposite to the source. Rack II comprises one or more planes. Each plane has a frame with covering plates and reference elements such as in rack I. Rack II may also comprise devices to identify each of the measurements, scattered radiation filters, holders for the recording means and a holder for a "gammameter" (which is described below).

The reference elements are made of a high density material (such as Pb or W) and are arranged so that the radiation emitted by the source traverses them before reaching the recording means. The reference elements can be rods, beads or similar objects, small beads being most preferred for the reasons set forth below. These reference elements are located on the plates that are fixed to the rack's frame.

The shielding mentioned above in the description of the "source assembly" can be a plate made of lead, having a thickness of, for example 4 mm, surrounding the frame of rack I, said arrangement having the purpose of absorbing radiation scattered in angles above and near 90 degrees through the first concrete layers traversed by radiation.

The device to identify each particular measurement may consist in a support fixture for letters made of an absorbent material (Pb, W, etc.) to identify the specific field work being performed, which support fixture stays unchanged during the field work, while a second support fixture containing a numbering system to identify each measurement increases by one unit upon each successive measurement. This device can be integrated into rack II in order to facilitate the procedure of identifying of each measurement, thus improving the prior art.

The scattered radiation filter can be housed in between both plates in rack II, so as to achieve an optimum ratio between the intensity of direct radiation and that of scattered radiation reaching the recording means, since said ratio affects the contrast of the image of the object being examined (for example steel bars) on the recording means. The composition and thickness of the elements of said scattered radiation filter are selected through the use of a simulation program, specially designed for this purpose (ref. 6).

The "gammameter" is a plate of lightweight material supporting several devices sensitive to radiation, whose purpose is to obtain remote readings of the radiation doses on different spots of the covered area as recorded by the recording means during measurements, thus permitting to assess the optimal irradiation time for the measurement.

Once the "source assembly" and rack II have been deployed, the radiation source is turned on and irradiation commences. In the case of a gamma radiation source, the radioactive tablet is moved to the desired position. In the "external source" mode, the tablet is positioned in a collimator made of absorbent material, which is part of the "source assembly", so that radiation may particularly "illuminate" the volume under study, within a solid angle approximately equal or slightly larger than the solid angle defined by the source and the area of the recording means. In the case of a gamma radiation source, in the "internal source" mode, the tablet is moved by means of an extension of the irradiation mechanism, which is introduced into a hole drilled into the piece under examination, thus allowing a measurement in the volume corresponding to the solid angle defined by the source and the area of the recording means.

Irradiation takes place during a specific period of time according to the doses indicated by the "gammameter", and to the table setting forth the relationship between irradiation time versus the doses for different combinations of sources and recording means.

Once the measurement has ended, if the recording means is of the cumulative type (radiographic plate, film or digital), which requires "off-line" reading, it is removed. A new recording means is conveniently set in place in rack II; the measurement numeral is increased by one unit; and a new measurement is carried out with the source in a new position, either changing the position of the "source assembly" or not.

After a given structural "sector" has been inspected, and the necessary number of measurements has been made, a tomographic determination is carried out. The analysis procedure, which is part of the method of the present invention, includes a computer program comprising the following steps:

a) Entering size and orientation data of the section of the piece being measured (beam, column, etc.), object of the tomographic analysis. A main coordinate system, fixed to the structure under study, is defined to which the results of the analysis will be referred.

b) Indicating which side of the piece under study the recording means has been placed on in each of the measurements.

c) Identifying the fiducial marks on the recording means. The program performs a least-square adjustment to determine with high accuracy the position of said fiducial marks in the coordinate system of the recording means. The accuracy achieved by means of this procedure is improved when the fiducial marks are circles or ellipses, corresponding to spherical reference elements (see below a note about the accuracy that can be achieved with this method). The position of the fiducial marks determines: i) the position of the source in each measurement with respect to the recording means and to the main coordinate system and, ii) the position of the recording means with respect to the main coordinate system and with respect to the position of the recording means in the rest of the measurements made on the same section of the structure.

d) Determining data pairs corresponding to the contour of the steel bar projections in different sections, called "contour pair". The number of required pairs depends on the orientation and changes in direction of the bar projections.

e) Calculating the "shadow cones" defined by the position of the source and each contour pair, obtained for all measurements performed for the same section of the piece under study.

f) Determining shadow cone intersections corresponding to actual bars, taking into account the "contour pairs" for the different cross-sectional measurements performed all along the piece under examination.

g) Producing a technical report with the tomography result, that is, the number, position and diameter of each bar in the examined sections.

This analysis procedure is characterized by and distinguished from the prior art in that it combines in a simple way the data resulting from different coordinate systems (the coordinate systems for each of the recording means) in a single main coordinate system fixed to the piece under study.

The use of the method of the present invention will now be described for particular cases, as non-limiting illustrative examples.

In a particular embodiment of the invention, the method is used for the tomographic determination of reinforcement bars in slabs or walls using a $^{192}$Ir source. The equipment comprises, in this case, a "source assembly" fixed to one of the faces of a slab or wall whose reinforcement bars are to be measured, and a "uniplanar" rack II fixed to the opposite side of the slab or wall. In general, although not always, measurements of slabs and walls are carried out in the "external source" mode.

Figure 2:
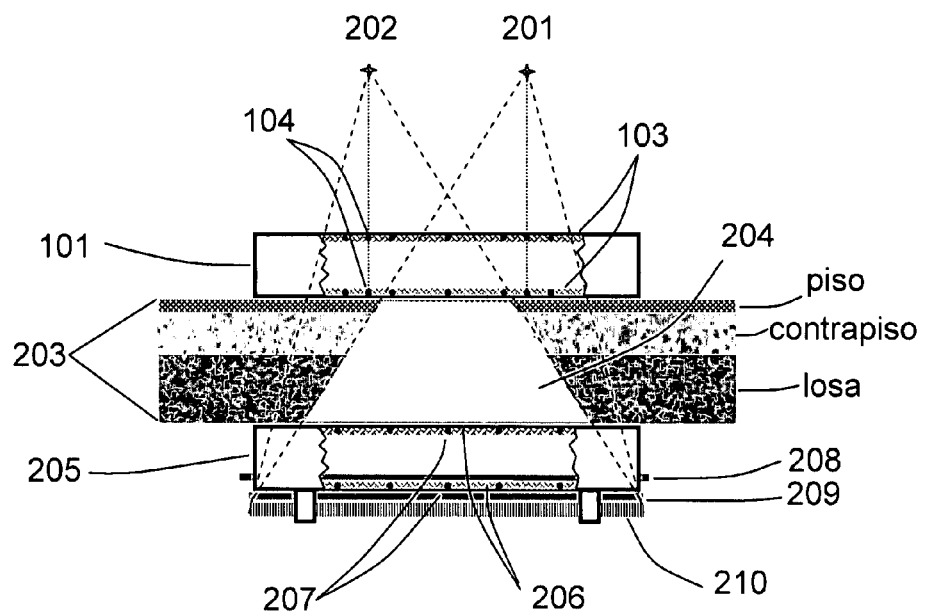
FIG. 2 is a cross-sectional diagram of an arrangement used for the study of reinforcement bars in slabs and walls, using an "external source"

An example of this embodiment for the analysis of a slab using an "external source" is illustrated in FIGS. 1 and 2. The "source assembly" is shown in FIG. 1 and comprises a rack I 101 consisting of a frame 102 and two plates 103, one upper and one lower plate, onto which reference elements 104 are attached in accurately preset positions; a source support composed of two columns 105, a crossmember 106, a collimator support 107 and a collimator 108. The size of this assembly corresponds to the experimental needs and conditions. The case shown in this example is prepared for use with radiographic plates, for example, of 35×43 cm, and, accordingly, the frame 102 of rack I 101 is, for example, of 39×49 cm. The two columns 105 are detachably inserted into the frame 102 of rack I 101. The columns 105 support a crossmember 106, which may be located at two preset heights. A support 107 for the collimator 108, into which the radioactive source is introduced, slides horizontally on the crossmember 106. The support 107 of the collimator 108 may be fixed to the crossmember 106 in different preset horizontal positions 109 by means of an anchoring bolt. The crossmember 106 crosses rack I 101 diagonally, passing through its center. The shielding 112 that may be used to shield tangential radiation and increase radiological protection is shown partially. The frame 102 and the crossmember 106 are preferably made of Al and the columns 105 are preferably made of steel.

The assembly may be attached to the slab or wall under study using different procedures. One of them comprises, for example, the use of two suction cups 110, attached on opposite sides of the frame 102 of rack I 101, fixing the whole assembly onto smooth floors or pavings; another procedure comprises the use of screws affixed in holes 111 drilled into frame 102 of rack I 101 for this purpose.

FIG. 2 shows a cross-sectional view of an arrangement adapted to be used to study a structure 203 consisting of a reinforced concrete slab, subfloor and floor, with an "external source", wherein rack I 101 is placed on structure 203 and rack II 205 is placed under said structure 203. For the analysis according to this arrangement, the source is located at both positions 201 and 202; said positions being selected by a calculation that takes into account thickness 203 and density, in this case, of the slab, subfloor and floor assembly. The horizontal and vertical positions of the source in both measurements of the same portion of the slab (or wall) must be determined so as to optimize the following conditions:

a) the largest possible effective inspection volume 204 should be covered in both measurements.
b) the largest possible effective recording area in the radiographic plate (placed inside housing 209) should be obtained, taking into account the sensitivity range of the plate and the difference of radiation paths incident between the borders and the center of the plate.
c) the duration of each measurement should be kept to a minimum.

In order to locate the source according to these conditions, rack I has two possible preset heights and four possible horizontal positions 109 at each side of the center of crossmember 106 separated by a preset distance of, in this example, 1 cm in the direction of crossmember 106.

Also shown in FIG. 2 is the assembly of reference elements (in this case, small beads) 104, in rack I 101, and 207, in rack II 205, inserted into plates 103 and 206, respectively. In the case of rack I 101, a pair of beads 104 may be placed on the vertical axis of each of the predetermined horizontal positions 109 in crossmember 106 for locating the source, in order to readily visualize the position of the source at each measurement by reading the respective fiducial marks on the recording means. Fiducial marks corresponding to reference elements allow for an accurate determination of the positions of the source and the recording means for each measurement with respect to a fixed coordinate system, which is common for all measurements carried out in the same section. The reference elements that are closest to the source and to the recording means are those that allow for said determination with the least error as regards to the positions of the source and the recording means, respectively.

FIG. 2 also shows an arrangement of the scattered radiation filter 208, of the recording means 209 (for example, a cassette with a radiographic plate and usual amplifying screens therein) and the gammameter 210 in contact with the rear side of the recording means. The upper side of the recording means is in contact with the filter 208. The space between lower and upper plates 206 is such that, once the recording means is arranged, it will remain at an optimum distance from the structure to be measured, which distance is determined by a simulation carried out with the program of Ref. 6.

The procedure for studying the reinforcement bars of slabs or walls consists in the first place, in fixing the "source assembly" on one of the sides of the structure under study by means of one of the above-mentioned alternative procedures. Then the collimator is placed in a first position 201 by moving it horizontally along crossmember 106 to one of the predetermined positions 109 and moving said crossmember vertically to one of the predetermined positions in columns 105, in such a way that position 201 corresponds to that indicated to meet the above mentioned conditions. Then the second rack II 205 is placed on the opposite side of the structure, using an unexposed recording means 209. In the following step, irradiation for a predetermined period of time is carried out (for example, according to the indication of the gammameter). At the end of this period of time the source is returned to its shielded container and the recording means 209, in case it is of the cumulative type (for example, radiographic plate, film or digital), thus requiring "off line" processing, is withdrawn for further processing.

This procedure is then repeated, placing the source in a second position 202, and a new recording means 209 is set in place, in a position similar to the former one. It is not necessary for the recording means positions to be exactly the same in both measurements (as it was in the previous art) because of the reference system of the present invention.

Finally, once the programmed measurements for the structure section under study have finished (in this particular example, two radiographic plates), the tomographic determination is carried out, following the procedure outlined above, in order to determine the number of steel bars, their diameter, condition and location inside the structure, by combining the information resulting from all the measurements.

Figure 3:
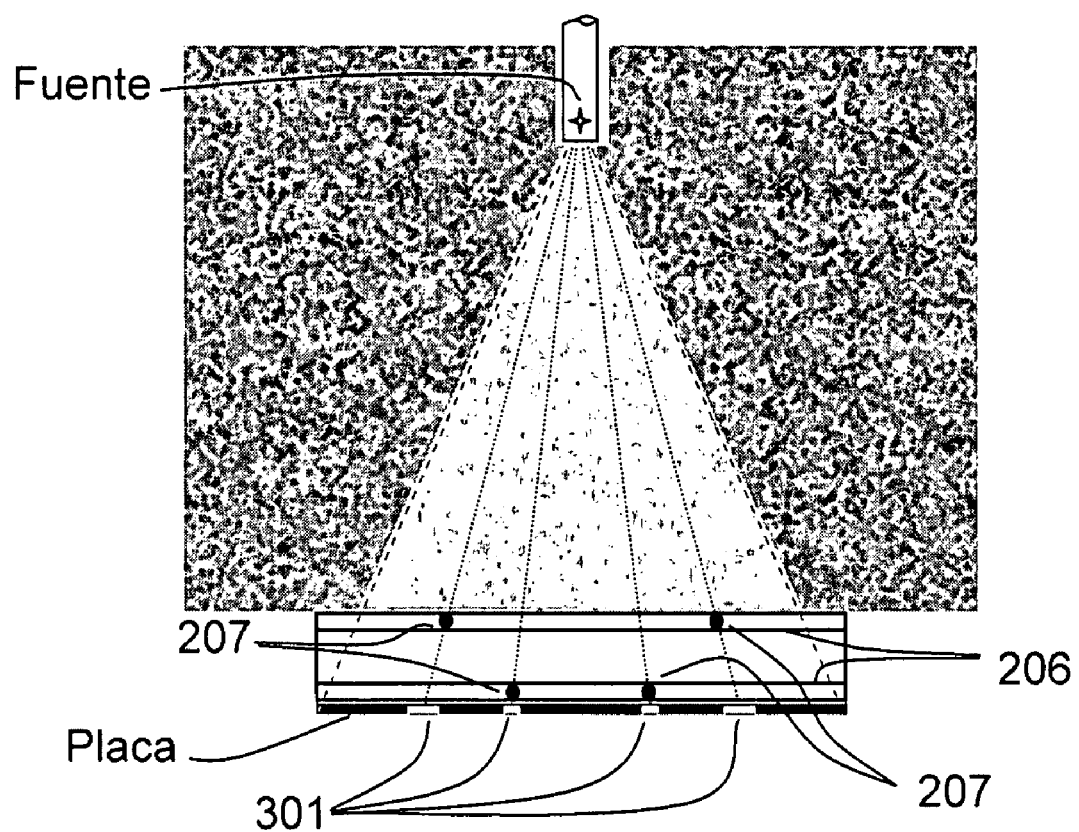
FIG. 3 is a cross-sectional diagram of an arrangement used for the study of reinforcement bars in reinforced concrete structures, using an "internal source"

FIG. 3 shows a cross-sectional diagram similar to that of FIG. 2 but with an arrangement that uses the "internal source" mode (see herein below). In this case rack I does not exist, and the method of the present invention applies using reference elements 207 (beads in this case) in plates 206 of rack II. The filter 208 and the "gammameter" 210 shown in FIG. 2 are not shown here for the sake of clarity, while the recording means is in this case a radiographic plate indicated with a black line with white intervals 301 simulating the fiducial marks or "shadows" produced by the absorption of radiation emitted by the source in the reference elements 207. The operator only measures and records the position of the rack with respect to some reference point in the structure. The positions of the source and the recording means can then be calculated by knowing the coordinates of the reference beads 207 and measuring the position of their images 301 on the radiographic plate.

As in the case of the "external source" mode, without moving the rack a second recording means is then placed on rack II and a new measurement is carried out with the source in a second position. The data from these two measurements, or more if it were the case, are then used to determine the position and size of the reinforcement bars in the slab. This procedure has the advantage of saving time and effort during field work and also allows to avoid errors and hence to achieve a greater accuracy, especially in those cases where simultaneous access to both sides of the structure is not possible, as is frequently the case for slabs or walls in which the source and the recording means are in different rooms. In these cases conventional measurement of the position of the source with respect to the recording means is not trivial.

In order to determine the positions of the source and the recording means (which is necessary for the tomographic determination of reinforcement bars) it is in principle enough to obtain images of two reference elements for each. In practice, however, it is convenient to arrange more than two reference elements and to obtain their corresponding fiducial marks in order to achieve greater accuracy, by averaging the results obtained for individual pairs and also because of the possibility that some of these marks may be superimposed to other marks in the plate, thereby making their interpretation difficult. The possibility of averaging independent values has the advantage of reducing reading errors as well as those errors derived from manufacturing tolerances regarding the predetermined position of the reference elements.

In another embodiment of the invention, the method is applied to the tomographic determination of reinforcement bars in beams or columns. In analogous manner as in the previous case, the equipment in this case comprises a "source assembly" fixed on one of the sides of the beam or column whose reinforcement bars should be measured, and a "uni-, bi- or tri-planar" rack II, fixed to another side or sides of the beam or column.

Figure 5A:
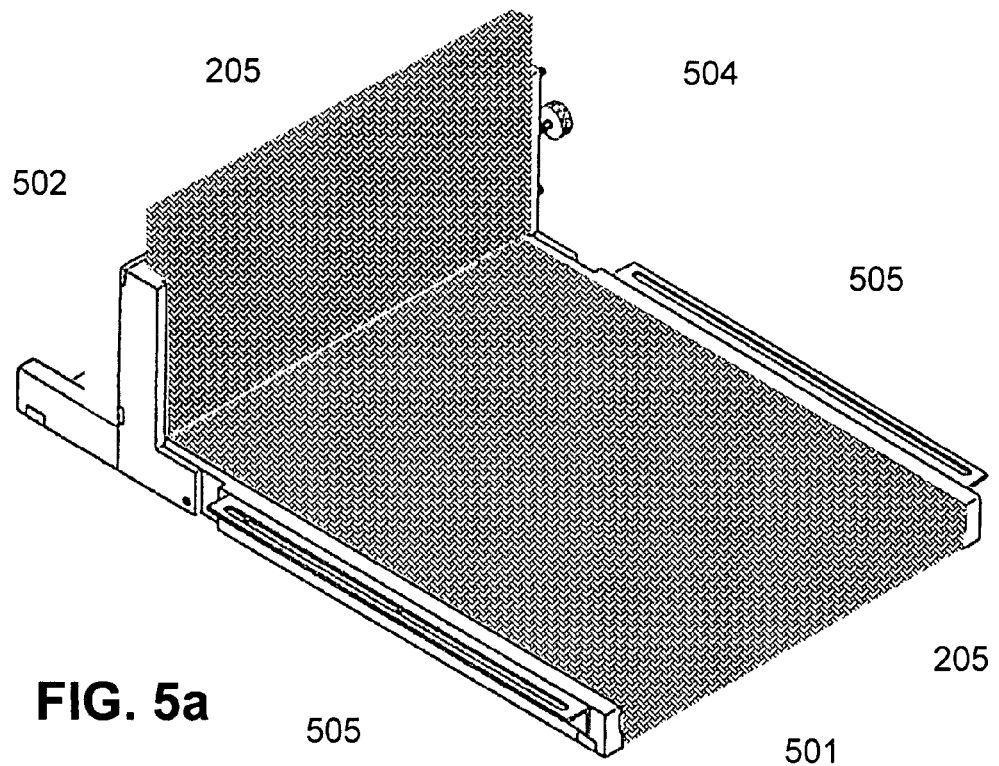
FIGS. 5(*a*), 5(*b*) and 5(*c*) are perspective views of the rack used for the study of steel reinforcement bars in beams and columns, in open and closed positions.
Figure 5B:
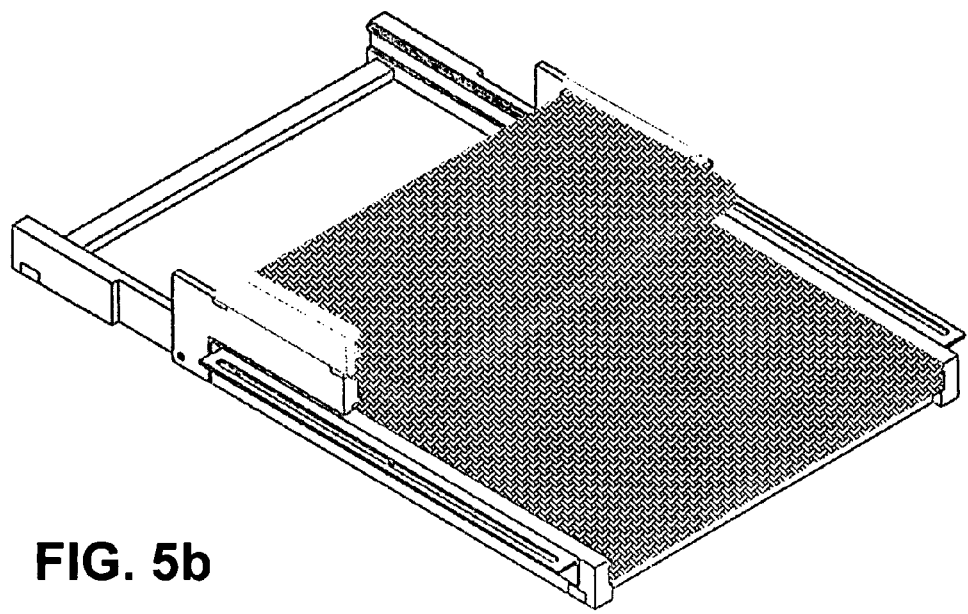
Figure 5C:
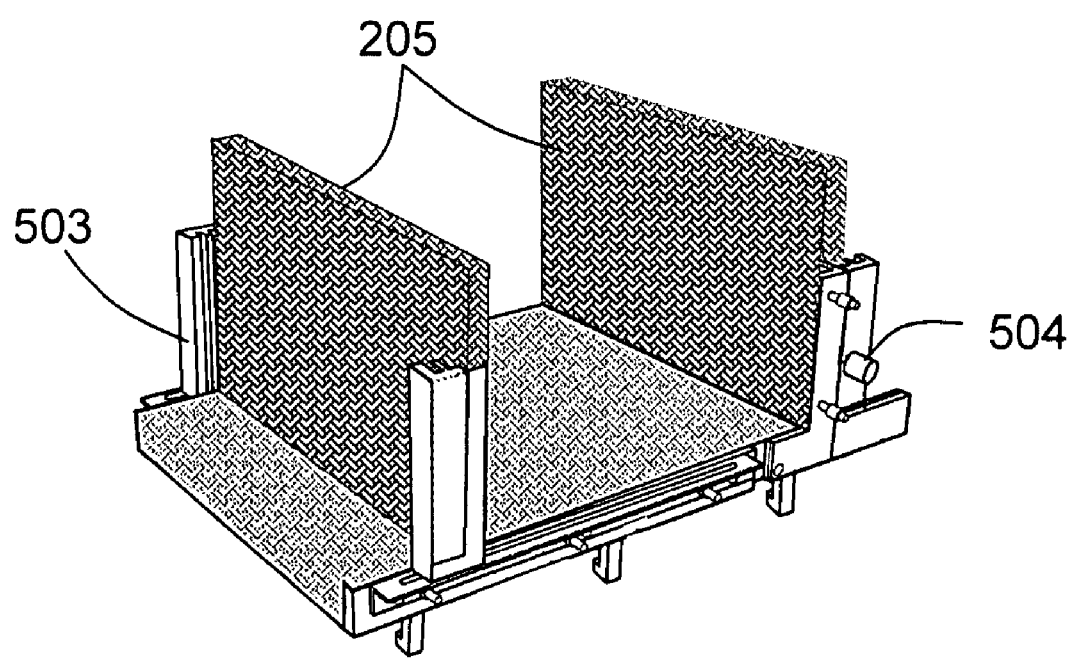
Figure 6:
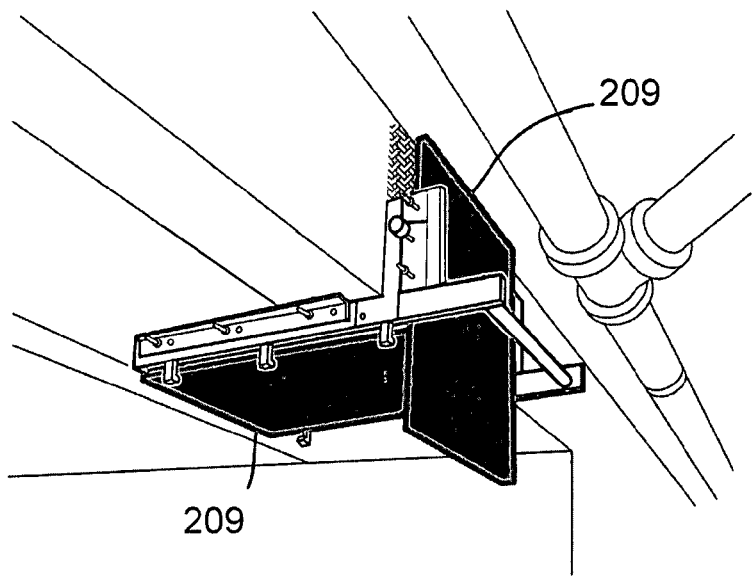
FIG. 6 shows the position of the rack on a beam.

An example of this embodiment, applied to the study of a central section of a beam, is illustrated in FIGS. 4, 5 and 6.

Figure 4A:
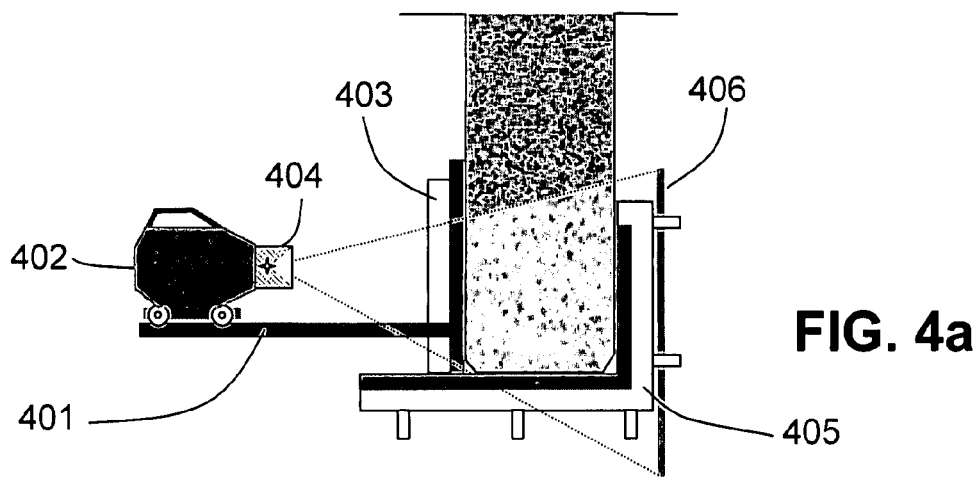
FIGS. 4(*a*), 4(*b*) and 4(*c*) illustrate two arrangements for the study of reinforcement bars in the lower central section of a beam and an arrangement for the study of reinforcement bars in a column.
Figure 4B:
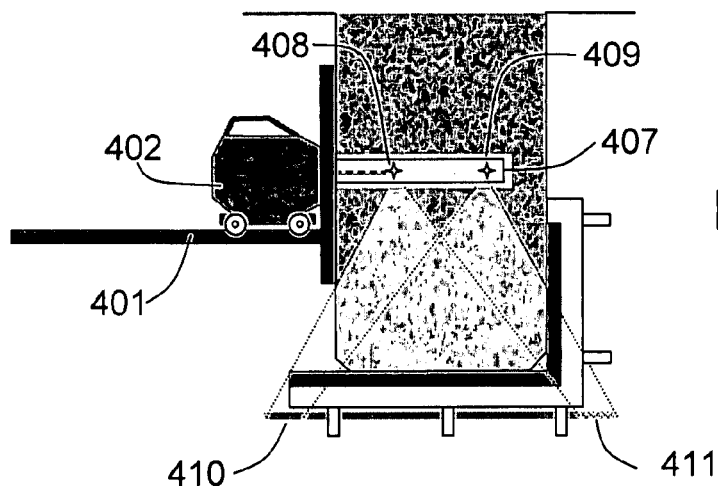
Figure 4C:
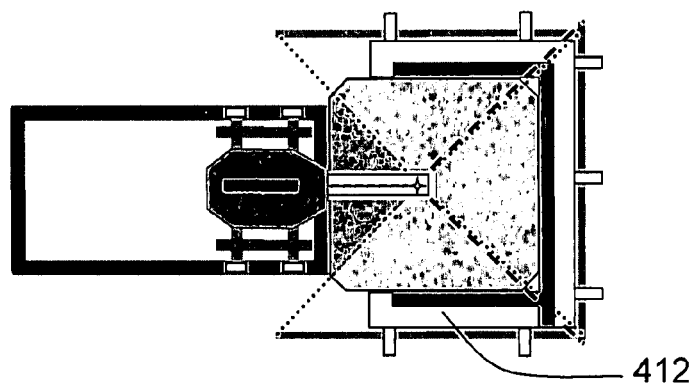

FIG. 4 shows schematically two possible arrangements for the study of a beam section and a column section, using a $^{192}$Ir radioactive tablet as a source. In (a) an arrangement of the "external source" mode is shown. The "source assembly" comprises a support 401 for the container/projector of source 402 with its source, fixed to a rack I 403 with a frame and two plates comprising reference elements (similar to rack I 101 in FIG. 1 and according to the description of the elements shown in FIG. 1). An optional shielding (not shown in FIG. 4). similar to the one shown as reference 112 in FIG. 1 can be added with the purpose of reducing the intensity of tangential radiation The collimator 404 allows to direct radiation in the desired direction (towards the right hand side in the figure) after the source is displaced from the inside of container 402 to the collimator 404 in order to start the measurement. The rack II 405 consists of two planes, each comprising a frame with plates, reference elements, room for a filter, a support for recording means and, optionally, a gammameter (see FIGS. 5a and 5b) in analogous manner to the description for rack II 205 in FIG. 2. Said rack is attached to the beam such that both planes remain in contact with two of the beam sides (opposite and adjacent to the side on which the source support is attached) and the intersection of both planes coincides with the edge of the beam opposed to the source side. In the case of "external source", in which the source is located as shown in FIG. 4(a), one or more measurements (with the source in different positions in the vertical and horizontal directions) are carried out with recording means 406, located in the recording means supports in the vertical and horizontal planes of rack II 405. In (b) a similar arrangement but in the "internal source" mode is shown, where the frame 403 and its associated elements are removed from the "source assembly", and the collimator 404 is replaced by an extension 407 consisting of a tube of suitable material of appropriate diameter (for example approximately 12 mm and 15 mm of internal and external diameter respectively) to allow the displacement of the source therein, which tube is introduced through a hole (for example of about 17 mm in diameter) drilled into one of the lateral sides of the beam at a certain distance from the lower side of the beam (for example about 28 cm if the source being used is $^{192}$Ir, and for example 50 cm if the source is $^{60}$Co). For example, the length of such tube and the depth of the orifice should be approximately equal to the thickness of the beam less approximately 10 cm. When using an "internal source", N measurements are preferably carried out, (where N is the integer greater and closest to A/10−1, being A the width of the beam section measured in cm). In a first measurement, the source is placed, for example, in position 408, at about 10 cm from the side of the beam through which the source is inserted and the recording means is placed into the supports of rack 405, preferably in position 410, such that its center lies opposite to position 408 of the source. In successive measurements the source and the center of the recording means are placed at, for example, 20, 30 . . . (A−10) cm from the side of the beam through which the source is inserted (positions 409 for the source and 411 for the recording means and successive positions). In (c) an arrangement similar to (b) in the "internal source" mode is shown, for the study of reinforcement bars in a column thicker than established by the applicable standards, for example "Testing concrete", British Standard 1881, part 205. Recommendations for radiography of concrete, 1986 (ref. 3). In this arrangement a $^{192}$Ir source is used, where an additional plane 412 is added to rack II (as shown in greater detail in FIG. 5(c)) and such plane is adjusted so that it contacts the side adjacent to the side through which the source is introduced (FIG. 4(c)). A hole is preferably drilled on the center of the side through which the source will be introduced if the distance between hole and adjacent sides is, for example, between 20 and 30 cm, or two holes are drilled otherwise, such that each hole is at a distance of, for example, between 20 and 30 cm from either of the sides adjacent to the source side (these values are increased by a factor of about 2.5 if a $^{60}$Co source is employed). In a first measurement the source is introduced, for example, 10 cm within the column. In the case of a single central hole, two recording means located opposite to each other on the planes adjacent to the side through which the source is introduced, and whose centers are opposed to the source, are simultaneously irradiated. Otherwise, a single recording means located at a distance of, for example, between 20 and 30 cm from the hole, on one of the sides adjacent to the side where the source is introduced, is irradiated. As many measurements as necessary are taken displacing the source, for example in 10 cm intervals, up to a depth equal to the dimension of the column in the direction parallel to the hole, less 10 cm. In each measurement the recording means (either one or more, in case of simultaneous measurements) is placed opposite to the source. The measurement(s) in which the source lies, for example, between 20 and 30 cm from the side opposite to the side through which the source is introduced, is (are) carried out placing a recording means on the side opposite to the side where the source was introduced. In the case of two holes, the procedure is repeated with the recording means located on the side opposite to that used in the first series of measurements.

FIGS. 5(a), 5(b) and 5(c) illustrate arrangements for rack II used in the study of beams and columns as described hereinbefore. FIGS. 5(a) and 5(b) illustrate two perpendicular planes, the main plane 501, and the secondary plane 502, fixed to each other, which can be collapsed so to adopt two alternate positions: i) an open position for use during measurement (FIG. 5(a)) and ii) a closed position for use during transportation (FIG. 5(b)). Additionally, another secondary plane 503 can be added which is perpendicular to the main plane 501, and which can slide on the main plane frame such that it contacts the free lateral side of the beam or column. Each of the planes 501, 502 and 503 are similar to the "uniplanar" rack II 205 of FIG. 2 and comprises, as well as the latter, a reference system, a housing for a scattered radiation filter, a support for the recording means and a support for a gammameter, such as was described hereinbefore (not all these elements are shown in FIGS. 5(a), 5(b) and 5(c) for the sake of clarity). The position of the centers of the recording means located on planes 501 and 502 can vary by a distance approximately equal to one length of the corresponding plane, whereas in the case of plane 503 this variation is restricted by the fact that one of the edges of the recording means located in the support in this plane is limited by the upper surface of the main plane. The length of the main plane of the prototype shown in FIG. 6 is determined by the application, and in the example it is, for example, approximately 50 cm, and can be extended using supplements. Also shown in FIG. 5(a) are metal straps 505 that provide a fixing means for rack II to the beam or column, and a screw 504 that is adjusted against the recording means located on plane 502, when the latter is in a vertical position (as in the case of FIGS. 4(a) and 4(b)) to prevent the recording means from sliding downwards.

FIG. 6 illustrates the position of a rack II with perpendicular planes in operation position on a beam with recording means 209 on the vertical and horizontal planes (gammameter not shown). The rack II is fixed to the beam or column by any of the alternate procedures described hereinbefore, such that the planes contact the sides of the beam or column and the intersection of planes 501 and 502 coincides with one of the edges of the beam or column.

The method of the present invention can also be applied to other studies of structures and other bodies opaque to visible light. Within the field of structures, mention should be made of flexible racks, with the attributes described hereinbefore, for the study of, for example, columns with non-rectangular cross section. The method of the invention can be applied to the study of beam laterals in order to determine the point where certain steel bars change direction in order to resist shear stress near beam supports, or also to the study of the upper sections of beams above beam supports, or of foundations and, in case the thickness of the piece so requires, the "internal source" mode can be applied. The method of the invention has also been used for the study of the inner metal structure of monuments and ornaments.

Figure 7:
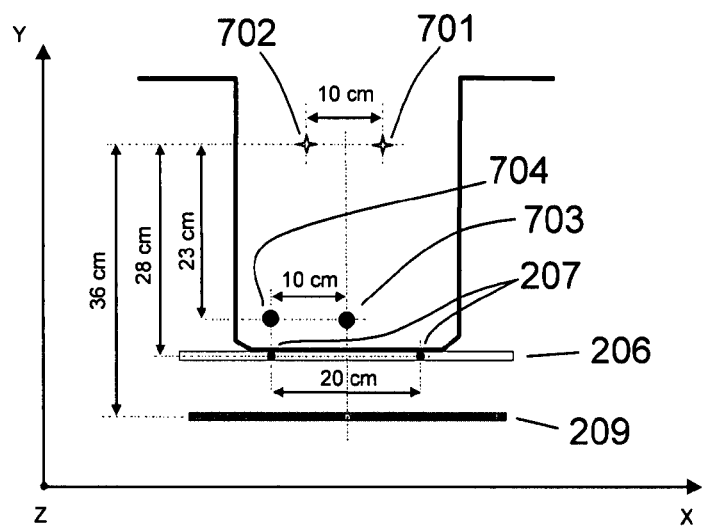
FIG. 7 is a diagram showing source, rebars, reference elements and plate arrangement assumed for calculating the errors involved in using the method of the present invention to determine the position of steel reinforcement bars in a structure.

FIG. 7 is a simplified scheme of a particular arrangement using an "internal source", which has been prepared to illustrate quantitatively the accuracy that can be achieved in the tomographic determination of reinforcement bars with the method of the present invention. For the purpose of this description, we only need to take into consideration two source positions 701 and 702, two steel bars 703 and 704, reference beads 207 incorporated to upper plate 206 of rack II, in positions (X,Y) indicated in FIG. 7 (lower plate 206 in rack II, filter 208 and gammameter 210 are not shown in the scheme for the sake of clarity). As described hereinbefore, these beads are very radiation-absorbent elements of a suitable diameter (preferably 2 mm). Under radiation these beads 207 create "shadows" or fiducial marks on the recording means 209, with the shape of ellipses that are clearer than the background. The reason the spherical shape for these reference elements is preferred is because the "shadow" of a sphere is a circle or an ellipse and these shapes can be adjusted using the least squares method and therefore their position can be determined with greater accuracy than is achievable using other shapes.

The accuracy with which the position and diameter of steel bars 703 and 704 can be determined, which constitute the unknown variable of the tomographic problem to be solved, depends on the manufacturing tolerances of all components comprising the reference system and also on the accuracy with which the centers of the bead images and the cross-sectional views of the shadows projected by the steel bars can be extracted from the recording means. The sources of error and its magnitudes, assumed for the purpose of the present calculation, are summarized in the first section of Table I.

The calculation of errors associated with the method of the present invention was carried out using realistic computer software that was specially developed for this purpose. Such software simulates the actual situation based on the nominal values for the positions of source, reference beads, steel bars and recording means, while it also takes into account the errors attributable to manufacturing tolerances and reading errors of fiducial marks on the plates. Those errors were estimated on a statistical base, assuming a normal distribution with certain standard deviations. The values and the coordinate system used in this calculation are shown in FIG. 7. The steel bars 703 and 704 are assumed to be parallel to the Z axis. Four beads 207 aligned in pairs with the Z axis are also assumed to be located, for example, 10 cm below and above the drawing plane.

The lower section of Table I summarizes the results, obtained by simulating two thousand measurements, of the achievable accuracy when using the present method in the determination of the position of unknown steel bars . For the sake of simplicity the calculation did not include the uncertainty of the position of the plate with respect to the rack. This magnitude can be determined very accurately using the fiducial marks of the beads inserted in the lower plate of the rack, which is very close to the plate. The above mentioned errors result basically from the assumption that the position of the source is apriori unknown. Therefore this calculation corresponds to a different arrangement to that described before in connection with FIGS. 1 and 2, in which the position of the source was considered as known beforehand. The calculation is therefore especially relevant for the "internal source"cases, for which the position of the source is not accurately known apriori. Despite the aforementioned approximations, the estimated errors in the method of the invention are considered representative for the applications of the invention.

TABLE I

|  |  | Errors (mm) |
|---|---|---|
| ASSUMPTIONS |  |  |
| manufacturing error in position X, Z of the beads |  | 0.5 |
| manufacturing error in the position Y of the beads |  | 0.5 |
| misalignment in X and Z of plates 206 (FIG. 2) |  | 1 |
| error in Y of position of plate at the reading place |  | 1 |
| Position adjustment error of fiducial marks |  | 0.5 |
| Adjustment error of the position of steel bar images |  | 0.5 |
| RESULTS |  |  |
| BAR 1 | error in X | 0.9 |
|  | error in Y | 3.9 |
| BAR 2 | error in X | 1.2 |
|  | error in Y | 4.6 |

The invention claimed is:

1. A method for improving tomographic determinations for the inspection of steel reinforcements in concrete structures said method comprising the steps of:
   a) irradiating said structure with penetrating radiation from different positions by means of a radiation source, and
   b) recording said radiation transmitted through said structure for the different positions of the radiation source in recording means; the method further comprising the steps of:
   i. defining and fixing a main coordinate system to the structure under study, to which the results of the analysis will be referred;
   ii. providing a reference system with a plurality of independently identified and individualized reference elements made of a high density radiation-absorbent material and contained in a rack, such reference elements being arranged in accurately known positions on a radiation source side and/or a recording means side of said structure in order to record fiducial marks on the recording means;

iii. identifying the above mentioned measurements;
iv. determining irradiation times; and
v. determining the position of the fiducial marks resulting from the reference elements in the racks, and then determining the position of both the radiation source and the recording means with respect to the structure under study, based on the position of such fiducial marks;
vi. determining the position and size of reinforcements within a structure based on information recorded on each of the recording means used for measurement by means of combining the data resulting from the different coordinate systems for each of the recording means in the single main coordinate system fixed to the structure under study.

2. The method according to claim 1, further comprising the step of providing a scattered radiation filter between the structure under examination and the recording means so as to achieve an optimum ratio between the intensity of direct radiation and that of scattered radiation reaching the recording means.

3. The method according to claim 1, providing means for determining the radiation time necessary to achieve maximum contrast.

4. The method according to claim 1, wherein the radiation source is an Xray or gamma-ray source.

5. The method according to claim 1, wherein the reference elements are bars, small spheres, beads or the like, within rigid or flexible support means.

6. The method according to claim 1, further providing support means for the reference elements. comprising one or more plates of a material with poor absorption of gamma radiation, selected from the group formed by plastic, acrylic, Luxite or similar materials.

7. The method according to claim 1, further comprising the step of drilling holes and introducing in said holes a radioactive source, to solve the determination of concrete pieces thicker than those covered by the applicable standards for the radioactive substances used for industrial X-ray determinations.

8. An arrangement for the inspection of steel reinforcements in concrete structures, which arrangement comprises for its application to the study of structures by means of an external source:
   a) a source of radiation capable of penetrating said structure;
   b) a support for the radiation source immovably attached to the structure being studied;
   c) recording means to record the transmitted radiation through such structure;
   d) a reference system with a plurality of reference elements independently identified and individualized, made of a high density material that absorbs radiation, which reference elements are arranged in accurately known positions;
   e) a first rack located between the source and the structure under study, immovably attached to said structure, which first rack comprises a reference system according to above paragraph d);
   f) a second rack immovably attached to said structure, which second rack comprises supports for the recording means and a reference system according to above paragraph d);
   g) identification means for measurements; and
   h) means to determine irradiation time comprising a device to remotely and continuously monitor the radiation dose applied to different spots on the recording means surface and determining the irradiation times comprising a rack with multiple radiation-sensitive devices, which device is located behind the recording means.

9. An arrangement for the inspection of steel reinforcements in concrete structures, which arrangement comprises for its application to the study of structures by means of an internal source:
   a) a source of radiation capable of penetrating said structure;
   b) a support for the radiation source immovably attached to the structure under study that is suited for using an internal source, that is, when the source is located within a hole drilled into the structure under study;
   c) recording means to record the transmitted radiation through such structure;
   d) a reference system with a plurality of reference elements independently identified and individualized, made of a high density material that absorbs radiation, which reference elements are arranged in accurately known positions;
   e) a rack immovably attached to said structure, which rack comprises supports for the radiation recording means and a reference system according to above paragraph d);
   f) identification means for measurements; and
   g) means to determine irradiation time comprising a device to remotely and continuously monitor the radiation dose applied to different spots on the recording means surface and determining the irradiation times comprising a rack with multiple radiation-sensitive devices, which device is located behind the recording means.

10. The arrangement according to claim 8 or 9, in that it comprises means to optimize the ratio of direct radiation to scattered radiation, thus improving image quality.

11. The arrangement according to claim 8, in that said second rack comprises one or more planes, immovably attached to said structure such that said planes are respectively parallel to the sides of said structure that are opposed or adjacent to the side of the structure on which said first rack is arranged.

12. The arrangement according to claim 9, in that said rack comprises one or more planes, immovably attached to said structure that are opposed or adjacent to the side of said structure on which said source is introduced.

13. The arrangement according to claim 8 or 9, wherein it comprises means to determine the irradiation time necessary to achieve maximum contrast.

14. The arrangement according to claim 8 or 9, wherein the optimal distance between the structure under study and the recording means is determined by means of calculations carried out with a program based on the Montecarlo or equivalent methods, capable of calculating the intensity and energy of the radiation reaching the recording means under the specific conditions of the structure under inspection.

15. The arrangement according to claims 8 and 9, wherein the rack, on which the recording means are arranged, comprises elements that preferentially attenuate scattered radiation traversing the structure under examination, which is particularly severe for reinforced concrete pieces, the nature and thickness of which are determined using simulations with a program based on the Montecarlo or equivalent methods, capable of calculating the intensity and energy of radiation traversing the structure under study under the specific conditions of each case.

16. The arrangement according to claim 8 or 9, wherein the rack, on which the recording means are arranged, consists of two planes and is fixed to the structure under study so that the intersection of both planes coincides with an edge of said structure, in such a way that the relationship between the reference elements on said planes and the structure under study is automatically defined.

17. The arrangement according to claim 16, wherein the planes are collapsible from an open position, in which the planes are arranged with respect to each other for use, to closed position, in which the planes are arranged parallel to each other to facilitate transportation.

18. The arrangement according to claim 8 or 9, wherein the rack, on which the recording means are arranged, consists of three planes perpendicular to each other, the third of which planes can be displaced with respect to the first plane, such that during use the planes are arranged against adjacent sides of the structure under study, such arrangement being particularly applicable to reinforced concrete beams and columns.

19. The arrangement according to claim 8, applied to the study of structures with parallel sides and of a great size as compared to the size of the equipment, as in the case of reinforcement bars within reinforced concrete slab, wherein the support of the source includes preset positions designed to maximize the effective volume under inspection as well as the accuracy of the three-dimensional analysis, as a function of the thickness of said structure and the type of radiation source and recording means being used, when multiple irradiations of a certain duration are being carried out.

20. A method for the inspection of steel reinforcements in concrete structures with parallel sides and of great size as compared to the size of the reinforcements such as reinforcement bars within a reinforced concrete slab, comprising the steps of:
    a) moving a support for a radioactive source along a crossmember support on a first rack to preset positions on one side of said structure;
    b) providing a support for a recording means on a second rack on the opposite side of said structure at a desired distance from the structure under study;
    c) supporting said crossmember diagonally with respect to the structure;
    d) automatically recording the information for tomographic analysis on said recording means without the need of intervention by an operator for subsequent use in computational analysis to determine information about said steel reinforcing elements.

21. A method for the three-dimensional analysis and measurements of steel reinforcing elements embedded in a solid structure under study, comprising the following steps:
    a) providing a radiation source on one side of the structure and a recording means on an opposite side of the structure;
    b) providing a reference system with a plurality of independently identified reference elements made of a high density radiation-absorbent material on one of the source side or recording side to eliminate the need for manual measurements and recordings;
    c) irradiating said structure with penetrating radiation,
    d) automatically creating fiducial elements on said recording means based on positions of said reference elements in said reference system;
    e) recording said radiation transmitted through said structure on the recording means;
    f) determining the location of said radiation source and recording means based on the fiducial elements.

* * * * *